United States Patent
Steele et al.

[11] Patent Number: 5,948,388
[45] Date of Patent: Sep. 7, 1999

[54] CHEWABLE SOFTGEL ORAL HYGIENE PRODUCT

[75] Inventors: Donald R. Steele; Rebecca Montes, both of Los Angeles, Calif.

[73] Assignee: Soft Gel Technologies, Inc., Los Angeles, Calif.

[21] Appl. No.: 09/096,808

[22] Filed: Jun. 12, 1998

[51] Int. Cl.[6] .................................. A61K 6/00; A61L 9/04
[52] U.S. Cl. .............................................. 424/44; 424/401
[58] Field of Search ........................... 424/44, 401; 514/2

[56] References Cited

U.S. PATENT DOCUMENTS

| | | | |
|---|---|---|---|
| 3,697,641 | 10/1972 | Ahrens | 424/38 |
| 3,899,593 | 8/1975 | Hammond et al. | 426/3 |
| 4,148,872 | 4/1979 | Wagenknecht et al. | 424/48 |
| 4,156,716 | 5/1979 | Wagenknecht et al. | 424/48 |
| 4,170,632 | 10/1979 | Wagenknecht et al. | 424/48 |
| 4,457,921 | 7/1984 | Stroz et al. | 424/180 |
| 4,508,713 | 4/1985 | Stroz et al. | 514/60 |
| 5,015,464 | 5/1991 | Strobridge | 424/48 |
| 5,075,291 | 12/1991 | DuRoss | 514/60 |
| 5,084,293 | 1/1992 | Todd, Jr. | 426/541 |
| 5,272,136 | 12/1993 | Mandai et al. | 514/27 |

FOREIGN PATENT DOCUMENTS 9704741  2/1997  WIPO .

*Primary Examiner*—Douglas W. Robinson
*Assistant Examiner*—Sandra Marshall
*Attorney, Agent, or Firm*—Evan M. Kent; Stewart L. Gitler; Martin P. Hoffman

[57] ABSTRACT

A chewable softgel formulation to deliver water soluble vitamins and supplements to improve dissolution time and availability. The formulation contains components design for the elimination and prevention of dental caries, bad breath, gingivitis and also inner ear infections.

15 Claims, No Drawings

CHEWABLE SOFTGEL ORAL HYGIENE PRODUCT

BACKGROUND OF THE INVENTION

A chewable softgel formulation to deliver water soluble vitamins and supplements to improve dissolution time and availability. The formulation contains components specifically designed for oral hygiene, including breath freshening, dental caries prevention, gingivitis prevention, and also inner ear infection prevention.

The formulation includes a powerful active ingredient which exhibits impressive antimutagenic activity. Applephenon, an apple extract an essential component of the encapsulated softgel formulation also functions as a breath neutralizing agent. It is also beneficial in the prevention of dental caries by preventing bacterial cells from adhering to tooth surfaces.

Various chewable formulations have been utilized in the past to inhibit plaque, neutralize bad breath and limit sugar quantity. None of the formulations are chewable softgel formulations which encapsulate a powerful ingredient applephenon, to combat various dental maladies.

The chewing gums and delivery vehicles of the prior art do not provide a chewable softgel which delivers the desired results.

It is an object of the present invention to produce a chewable softgel formulation to deliver water soluble vitamins and/or supplements.

It is a further object of the present invention to produce a chewable softgel formulation that is designed for oral hygiene, including breath freshening, dental caries prevention, gingivitis prevention and inner ear infection prevention.

It is a further object of the present invention to produce a chewable softgel formulation that is sugar fee and fat free.

SUMMARY OF THE INVENTION

The invention addresses a chewable softgel formulation including a hydrogenated starch hydrolysate; glycerin; xylitol; calcium ascorbate; water; zinc ascorbate; citric acid; flavoring and an apple extract. The formulation is sugar free, fat free and is designed for improved oral hygiene in a chewable softgel structure. Various flavorings such as strawberry, lemon, orange, citrus, or the like, are preferred for the chewable softgel product.

DETAILED DESCRIPTION OF THE INVENTION

A chewable softgel formulation including:
about 2.3 to about 2.4 wt % citric acid;
about 46.4 to about 48.4 wt % hydrogenated starch hydrolysate;
about 18.4 to about 19.2 wt % glycerin; about 14.7 to about 15.3 wt % xylitol; about 9.3 to about 9.7 wt % calcium ascorbate;
about 6.1 to about 6.3 wt % water; about 0.30 to about 0.32 wt % zinc ascorbate; about 0.53 to about 0.56 wt % flavoring; and
about 0.0989 to about 0.101 wt % an apple extract. The formulation is fat free and sugar free in its preferred form. The components form a chewable softgel that contains an active apple extract that is loaded with polyphenols to aid in the elimination or prevention of bad breath, dental caries, gingivitis and also, inner ear infections.

A preferred apple extract is Applephenenon™, sold by Nikka Whisky Distilling Co., Ltd. of Japan.

Preferred flavorings include strawberry, orange, lemon, citrus and combinations thereof.

A particularly preferred composition includes by weight:

| | |
|---|---|
| calcium ascorbate | 46.8926mg |
| zinc ascorbate | 1.5628mg |
| xylitol | 74.2458mg |
| citric acid | 11.7256mg |
| glycerin | 92.6634mg |
| water | 30.6417mg |
| flavoring | 2.6970mg |
| apple extract | 0.4985mg |
| hydrogenated starch hydrolysate | 234.4726mg |

The acceptable ranges for the components are approximately $+/\_2\%$ of the preferred composition.

As discussed, the product is unique in that it is a chewable softgel providing a delivery system for water soluble ingredients. The formulation is an unique combination of ingredients that help promote overall dental hygiene.

It is to be understood that the invention is not to be limited to the exact compositions or methods, or embodiments described, as obvious modifications and equivalents will be apparent to one skilled in the art, and the invention is limited only by the full scope which is accorded to the appended claims.

We claim:

1. A chewable dental caries prevention softgel composition comprising:
   a) hydrogenated starch hydrolysate;
   b) Glycerin;
   c) xylitcol;
   d) calcium ascorbate;
   e) citric acid;
   f) water;
   g) zinc ascorbate;
   h) apple extract; and
   i) flavoring.

2. The chewable dental caries prevention softgel composition as claimed in claim 1, wherein said composition is sugar free.

3. The chewable dental caries prevention softgel composition as claimed in claim 1, wherein said composition is fat free.

4. The chewable dental caries prevention softgel composition as claimed in claim 1, wherein said composition is sugar free and fat free.

5. The chewable dental caries prevention softgel composition as claimed in claim 1, wherein said flavoring is strawberry, lemon, orange, citrus or mixtures thereof.

6. The chewable dental caries prevention softgel composition as claimed in claim 1, wherein said hydrogenated starch hydrolysate is about 46.4–48.4 wt % of said composition.

7. The chewable dental caries prevention softgel composition as claimed in claim 1, wherein said glycerin is about 18.4–19.2 wt % of said composition.

8. The chewable dental caries prevention softgel composition as claimed in claim 1, wherein said xylitol is about 14.7–15.3 wt % of said composition.

9. The chewable dental caries prevention softgel composition as claimed in claim 1, wherein said calcium ascorbate is about 9.3–9.7 wt % of said composition.

10. The chewable dental caries prevention softgel composition as claimed in claim 1, wherein said citric acid is about 2.3–2.4 wt % of said composition.

11. The chewable dental caries prevention softgel composition as claimed in claim 1, wherein said water is about 6.1–6.3 wt % of said composition.

3

12. The chewable dental caries prevention softgel composition as claimed in claim 1, wherein said zinc ascorbate is about 0.30–0.32 wt % of said composition.

13. The chewable dental caries prevention softgel composition as claimed in claim 1, wherein said apple extract is about 0.0989–0.101 wt % of said composition.

4

14. The chewable dental caries prevention softgel composition as claimed in claim 1, wherein said flavoring is about 0.53–0.56 wt % of said composition.

15. A chewable sugar free, fat free dental caries prevention softgel composition comprising apple extract.

\* \* \* \* \*